(12) United States Patent
  Rexach et al.

(10) Patent No.: US 12,695,968 B2
(45) Date of Patent: Jul. 28, 2026

(54) TOILET BIOMETRIC DATA COLLECTION DEVICE

(71) Applicant: Kohler Co., Kohler, WI (US)

(72) Inventors: Rafael Rexach, Sheboygan, WI (US); Jiunntyng Chen, Kohler, WI (US)

(73) Assignee: Kohler Co., Kohler, WI (US)

( * ) Notice: Subject to any disclaimer, the term of this patent is extended or adjusted under 35 U.S.C. 154(b) by 150 days.

(21) Appl. No.: 18/230,932

(22) Filed: Aug. 7, 2023

(65) Prior Publication Data

US 2024/0056663 A1     Feb. 15, 2024

Related U.S. Application Data

(60) Provisional application No. 63/396,842, filed on Aug. 10, 2022.

(51) Int. Cl.
   *H04N 23/54*        (2023.01)
   *A61B 5/1172*       (2016.01)
       (Continued)

(52) U.S. Cl.
   CPC ........... *H04N 23/54* (2023.01); *A61B 5/1172* (2013.01); *G06V 40/10* (2022.01); *H02J 7/342* (2020.01); *H02J 7/50* (2026.01)

(58) Field of Classification Search
   CPC ... H04N 23/54; A61B 5/1172; A61B 2505/07; A61B 2560/0214; A61B 2560/0406; A61B 2562/227; A61B 5/6891; A61B 5/20; G06V 40/10; H02J 7/0013; H02J 7/342; G01N 21/25; G01N 21/84; G01N 33/483; G01N 2021/177; E03D 9/08; G16H 10/60
       (Continued)

(56) References Cited

U.S. PATENT DOCUMENTS

| 4,118,003 A | 10/1978 | Dillow | |
| 4,797,820 A | * 1/1989 | Wilson | ................. G05D 7/0635 |
| | | | 239/69 |

(Continued)

FOREIGN PATENT DOCUMENTS

| CN | 104969068 B | * 6/2019 | ......... G01N 21/8483 |
| DE | 102008030533 B4 | * 7/2011 | ............... E03D 9/08 |

(Continued)

OTHER PUBLICATIONS

Energizer Toilet Light Motion Sensor, Toilet Night Light; Jul. 12, 2022; 11 pages; https://www.amazon.com/Energizer-20-Color-Changing-Activated-54845/dp/B08ZJW33B9.

(Continued)

*Primary Examiner* — Lori L Baker

(74) *Attorney, Agent, or Firm* — Husch Blackwell LLP

(57)     ABSTRACT

A biometric data collection device for a toilet includes a first compartment, a second compartment, and a bridge. The first compartment includes a first circuit board. The second compartment includes a second circuit board. The bridge is coupled to the first compartment and the second compartment and is configured to be supported by a rim of the toilet so that the first compartment is inside of a bowl of the toilet and the second compartment is outside of the bowl of the toilet. The bridge is changeable in length to fit different widths of the rim.

18 Claims, 14 Drawing Sheets

(51) Int. Cl.
  *G06V 40/10*    (2022.01)
  *H02J 7/34*    (2006.01)
  *H02J 7/50*    (2026.01)
(58) Field of Classification Search
  USPC .......................................................... 4/661
  See application file for complete search history.

(56)        References Cited

U.S. PATENT DOCUMENTS

| | | | | |
|---|---|---|---|---|
| 4,934,000 | A * | 6/1990 | Freedman ............... | E03C 1/052 |
| | | | | 4/615 |
| 5,720,054 | A | 2/1998 | Nakayama et al. | |
| 6,446,875 | B1 * | 9/2002 | Brooks ..................... | E03C 1/05 |
| | | | | 236/12.12 |
| 6,641,305 | B2 * | 11/2003 | Wang ..................... | G01K 13/02 |
| | | | | 374/170 |
| 6,925,661 | B1 * | 8/2005 | Anger ................ | G05D 23/1393 |
| | | | | 4/541.2 |
| 6,997,064 | B2 * | 2/2006 | Bird .................... | G01F 15/0755 |
| | | | | 73/861.75 |
| 7,032,435 | B2 * | 4/2006 | Hassenflug ............... | G01F 1/28 |
| | | | | 73/40 |
| 7,124,452 | B1 * | 10/2006 | Bauza .................... | G01K 1/143 |
| | | | | 374/E1.019 |
| 7,832,030 | B2 | 11/2010 | Nunez et al. | |
| 8,686,863 | B2 | 4/2014 | Heller | |
| 8,802,442 | B2 * | 8/2014 | Wheeldon ............. | G01N 21/75 |
| | | | | 436/66 |
| 8,893,320 | B2 * | 11/2014 | Klicpera ............... | G01F 15/024 |
| | | | | 4/615 |
| 9,841,321 | B2 * | 12/2017 | Pastore ................... | G01J 3/28 |
| 9,863,967 | B1 * | 1/2018 | Hall ................... | G01N 21/6428 |
| 9,867,513 | B1 | 1/2018 | Hall et al. | |
| 10,494,803 | B2 | 12/2019 | Sonovani | |
| 10,760,978 | B2 | 9/2020 | Zhou | |
| 10,779,768 | B2 | 9/2020 | Han et al. | |
| 10,921,310 | B2 | 2/2021 | Mostafa et al. | |
| 11,064,886 | B2 | 7/2021 | Prokopp | |
| 11,131,087 | B2 | 9/2021 | Sonovani | |
| 11,213,234 | B1 | 1/2022 | Lichtman et al. | |
| 11,287,415 | B2 | 3/2022 | Barakat et al. | |
| 11,313,795 | B1 | 4/2022 | Yan et al. | |
| 12,318,173 | B2 * | 6/2025 | Russek-Sobol .... | A61B 5/14551 |
| 2002/0007510 | A1 | 1/2002 | Mann | |
| 2003/0066340 | A1 * | 4/2003 | Hassenflug ............... | G01F 1/28 |
| | | | | 73/46 |
| 2003/0233885 | A1 * | 12/2003 | Bird ...................... | G01F 15/003 |
| | | | | 73/861 |
| 2005/0261605 | A1 | 11/2005 | Shemer et al. | |
| 2008/0028505 | A1 | 2/2008 | Penn | |
| 2008/0148476 | A1 | 6/2008 | Lin | |
| 2009/0216099 | A1 | 8/2009 | Kim | |
| 2009/0249533 | A1 | 10/2009 | Sawalski et al. | |
| 2011/0051125 | A1 | 3/2011 | Kim | |
| 2013/0085409 | A1 | 4/2013 | Heller | |
| 2014/0135646 | A1 | 5/2014 | Heller | |
| 2016/0041565 | A1 | 2/2016 | Edwards | |
| 2016/0278705 | A1 | 9/2016 | Han et al. | |
| 2017/0022536 | A1 | 1/2017 | Velazquez et al. | |
| 2017/0322197 | A1 | 11/2017 | Hall et al. | |
| 2018/0042386 | A1 | 2/2018 | Hall et al. | |

| | | | | |
|---|---|---|---|---|
| 2018/0149666 | A1 * | 5/2018 | Hall ........................ | G01N 33/94 |
| 2018/0184906 | A1 | 7/2018 | Prokopp | |
| 2018/0188231 | A1 | 7/2018 | Barakat et al. | |
| 2018/0253715 | A1 | 9/2018 | Loeffler et al. | |
| 2019/0277710 | A1 | 9/2019 | Zhou | |
| 2019/0369085 | A1 | 12/2019 | Tan et al. | |
| 2020/0015791 | A1 | 1/2020 | Mccord et al. | |
| 2020/0100725 | A1 | 4/2020 | Temanson et al. | |
| 2020/0100771 | A1 * | 4/2020 | Attar ......................... | G01J 3/42 |
| 2020/0268303 | A1 | 8/2020 | Oliva | |
| 2021/0074390 | A1 | 3/2021 | Peesapati et al. | |
| 2021/0134464 | A1 * | 5/2021 | Kasai ...................... | G06F 18/24 |
| 2021/0169345 | A1 * | 6/2021 | Wasson .............. | G01N 21/3577 |
| 2021/0180713 | A1 | 6/2021 | Mariano | |
| 2021/0246643 | A1 | 8/2021 | Sonovani | |
| 2021/0386408 | A1 | 12/2021 | Attar | |
| 2022/0025093 | A1 | 1/2022 | Sgolastra et al. | |
| 2022/0049867 | A1 * | 2/2022 | Rexach ................... | F24F 7/003 |
| 2022/0081887 | A1 | 3/2022 | Sonovani | |
| 2022/0086347 | A1 | 3/2022 | Mallegowda et al. | |
| 2022/0087613 | A1 * | 3/2022 | Rexach .............. | A61B 5/02405 |
| 2022/0099660 | A1 * | 3/2022 | Goldman ............. | G01N 21/314 |
| 2022/0120071 | A1 | 4/2022 | Sonovani | |
| 2022/0151510 | A1 | 5/2022 | Kashyap et al. | |
| 2022/0170906 | A1 | 6/2022 | Barakat et al. | |
| 2022/0211354 | A1 | 7/2022 | Kashyap et al. | |
| 2022/0233848 | A1 | 7/2022 | Gad et al. | |
| 2024/0198328 | A1 * | 6/2024 | Nagarajan ............ | G01N 33/493 |
| 2025/0164506 | A1 * | 5/2025 | Karaoglu ........... | A61B 10/0051 |

FOREIGN PATENT DOCUMENTS

| | | | | |
|---|---|---|---|---|
| EP | 1170424 | A2 * | 1/2002 | ............... E03C 1/05 |
| EP | 1323872 | A1 * | 7/2003 | ........... E03C 1/0409 |
| EP | 3506834 | B1 * | 8/2021 | ........ G01N 21/6486 |
| JP | H0715001 | U | 3/1995 | |
| JP | 2002071636 | A * | 3/2002 | ........... G01J 3/0264 |
| JP | 2018528413 | A | 9/2018 | |
| JP | 2020516422 | A | 6/2020 | |
| JP | 2021507737 | A | 2/2021 | |
| WO | 1998003740 | A1 | 1/1998 | |
| WO | WO-2007065177 | A1 * | 6/2007 | ........... F21V 33/004 |
| WO | 2009035599 | A1 | 3/2009 | |
| WO | WO-2015138028 | A2 * | 9/2015 | ........... G01J 3/0264 |
| WO | WO-2016135735 | A1 * | 9/2016 | ........... G01J 3/2803 |
| WO | 2021175944 | A1 | 9/2021 | |
| WO | 2021205345 | A1 | 10/2021 | |
| WO | 2021240865 | A1 | 12/2021 | |
| WO | 2021246256 | A1 | 12/2021 | |
| WO | 2022122421 | A1 | 6/2022 | |

OTHER PUBLICATIONS

LED Toilet Bowl Light Komire Motion Activated Toilet Light; Jul. 12, 2022, 11 pages; https://www.amazon.com/Detection-Activated-Komire-Washroom-Operated/dp/B07JDTGW41.
European Official Action dated Feb. 12, 2025 issued in corresponding European application.
Japanese Official Action dated Mar. 24, 2026 issued in corresponding Japan application.
European Official Action dated May 28, 2026 issued in corresponding European application.

* cited by examiner

S101

Adjust a length of a bridge between a first compartment and a second compartment.

S103

Fit the bridge of the collection device to a rim of the toilet.

S105

Collect data at the first compartment of the collection device.

S107

Analyze the data.

S109

Identify a user associated with the data.

S111

Storing the data with an indicator of the user.

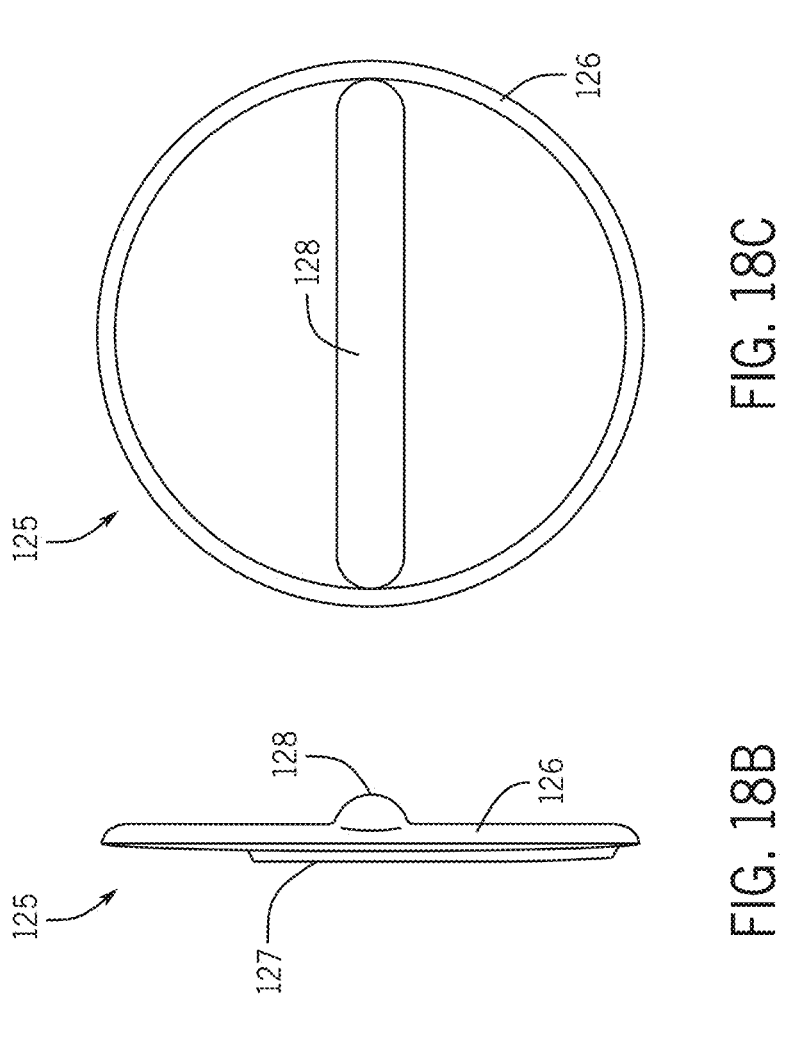
FIG. 18C
FIG. 18B
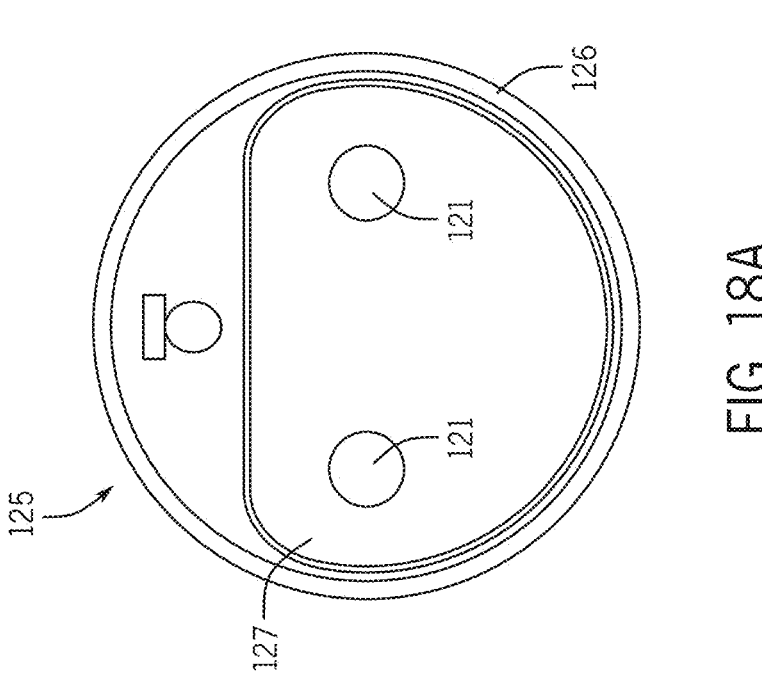
FIG. 18A

TOILET BIOMETRIC DATA COLLECTION DEVICE

This application claims priority benefit of Provisional Application No. 63/396,842 filed Aug. 10, 2022, which is hereby incorporated by reference in its entirety.

FIELD

The present application relates to a data collection device for a toilet, and more specifically, a structure for mounting the data collection device to a rim of the toilet.

BACKGROUND

The analysis of urine and feces may help in diagnosing health conditions. These health conditions may range from poor nutrition to cancer. The health conditions may include infection from viruses, bacteria, parasites or other microbial entities that may be harmful to the human body. Urine is also a valuable source of diagnostic information for health conditions. Examples include urinary tract infection, kidney infection or other kidney disease, and diabetes.

In some examples, urine and feces may be placed in a container and transported to a laboratory for analysis. This technique is time consuming and expensive. Techniques for at home analysis may reduce some of these downfalls of laboratory testing.

BRIEF DESCRIPTION OF THE DRAWINGS

Exemplary embodiments are described herein with reference to the following drawings, according to an exemplary embodiment.

FIGS. 18A-C illustrates a swappable pad for the data collection device.

DETAILED DESCRIPTION

Electronic devices inside a toilet bowl or near the rim of the toilet face hazardous conditions. Water and urine inevitably come in contact with the electronic device. Any water and urine that leaks inside the electronic device could wreak havoc on the electronic device. The electronic device should be substantially airtight and hermetically sealed. The housing of the electronic device may be formed of a hydrophobic material to repel water and urine.

The mounting structure that secures the electronic device to the rim of the toilet could also be susceptible to water and urine. Any moving parts of the mounting structure may also be particularly at risk to liquid. Also, the protein in urine may dry and become sticky and possibly be caked on moving parts. For example, a screw clamp may become unusable when exposed to drying urine.

The following embodiments include techniques for securing the electronic device to the rim of the toilet with minimal moving parts. Toilets, and specifically toilet rims, are available in a variety of sizes and widths. In addition, the width of the toilet rim may vary around the circumference of the toilet. Thus, the data collection device may be adjustable to fit the various sizes of toilet rims. In the first embodiment, a spring loaded sleeve allows the collection device to adjust to various rim sizes. In a second embodiment, a modular extender may be interchangeable to accommodate different rim sizes. In a third embodiment, the collection device may be flexible and confirm to the size of the rim.

Figure 1:
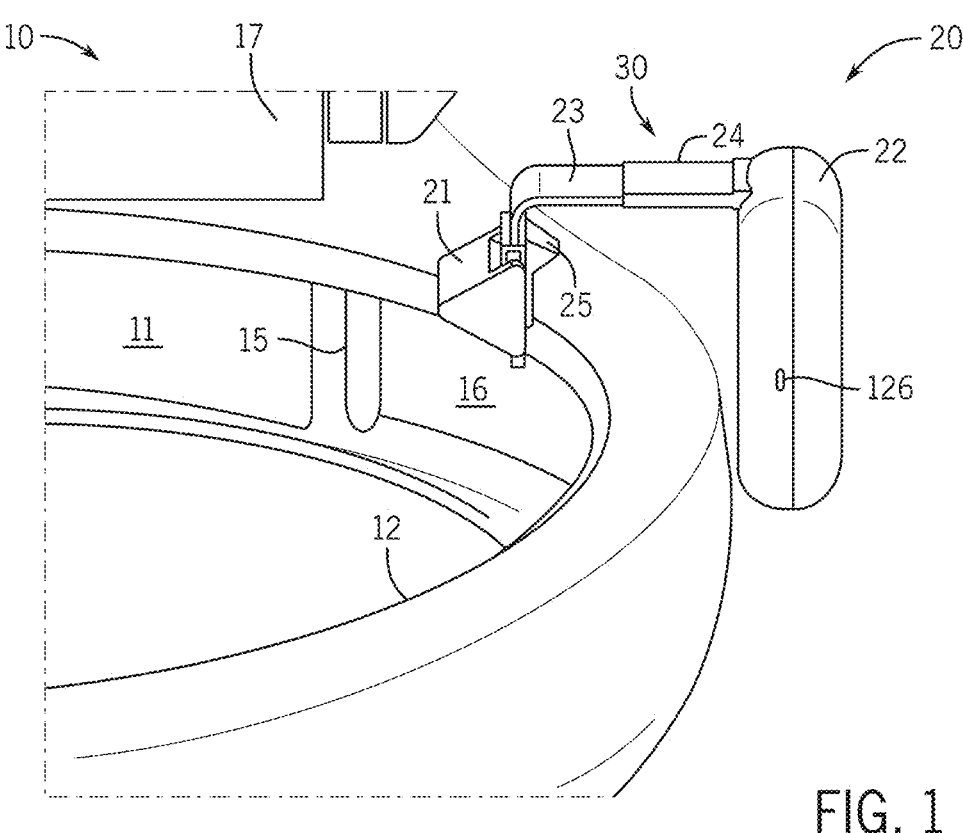
FIG. 1 illustrates toilet data collection device in an unmounted position.

FIG. 1 illustrates toilet data collection device 20 in an unmounted position with respect to a toilet 10. The toilet 10 may include a rim 12 around a bowl 11. The data collection device 20 may include a first compartment 21 and a second compartment 22. The first compartment 21 is coupled to the second compartment 22 by a bridge 30. Additional, different, or fewer components may be included.

The bridge 30 includes an outer extender 24 and an inner extender 23 as sleeves such that the inner extender 23 fits within the outer extender 24. The inner extender 23 may be coupled to the first component 21. The outer extender 24 may be coupled to the second component 22. A spring inside the outer extender 24 may be configured to push the inner extender 23 to slide farther within the outer extender 24. The spring may pull the inner extender 23 with respect to the outer extender 24. The spring may pull the inner extender 23 toward the rim 12. The spring may be a constant force spring should that the force placed on the inner extender 23 and/or the outer extender 24 is constant. Other examples may include progressive springs where the force applied by the spring is proportional to the relative distance between the inner extender 23 and the outer extender 24. The progressive spring or springs includes a spring constant that is variable depending on the relative position of the inner extender 23 and outer extender 24. In one alternative, the inner extender 23 and/or the outer extender 24 includes a ratcheting device that allows the inner extender 23 and the outer extender 24 to be pressed together but not a part. The ratcheting mechanism may be released via a release button.

The inner extender 23 and/or the first component 21 may include a bumper or grip 25 configured to press against the rim 12 and hold the data collection device 20 to the toilet 10. The user may manually press the inner extender 23 and the outer extender 24 toward one another to cause the grip 25 to contact the rim 12 and hold the data collection device 20 to the toilet 10.

The toilet 10 may include a variety of shapes and configurations for the base of the toilet 10 supporting the bowl 11 and rim 12. It should be noted that various components of the toilet may be made of a vitreous material such as clay. It should be noted that various components of the toilet may be polymeric and/or over molded or otherwise fixed to the toilet. The toilet disclosed herein may have a wide variety of skirted toilet configurations, and all such configurations are intended to be encompassed herein. The following description of various toilet features is therefore intended as illustration only of one possible embodiment, and it should be understood by those reviewing the present description that similar concepts or features may be included in various other embodiments.

The base of the toilet 10 may include any suitable shape that is configured to form the bowl 11 having an opening formed by the rim 12 at the top of the opening. The base may also be configured to include a plurality of walls having varying shapes that together form a bowl having an opening formed by a rim. The wall of a pedestal supporting the base may extend downward and/or rearward from the bowl 11 to form a lower portion configured to support the toilet 10.

The base may also include a top member that extends between two sides of the wall (or between two opposing walls) and is provided rearward (or behind) the bowl 11, wherein the top member forms a plateau for supporting a seat assembly 17. For example, the top member may include one or more than one opening, wherein each opening is configured to receive a fastening device (e.g., bolt, screw, etc.) to couple (e.g., attach) the seat assembly 17 to the top member of the base. As another example, the top member may include one or more than one fastening device (e.g., bolts, recessed nuts, etc.) integrally formed therein (i.e., already provided connected or coupled to the base), wherein the fastening device may be used to couple or secure at least a portion of the seat assembly 17. The seat assembly 17 may include a hinge, hinge shoulders configured to receive a fastener, a seat coupled to the hinge and a cover coupled to the hinge.

The bowl 11 may be configured to include a receptacle (e.g., sump) and an outlet opening, wherein the water and waste is collected in the receptacle until being removed through the outlet opening, such as upon activation of an actuator (e.g., lever, motor). The base may also include a base internal passageway, such as a trapway, that connects the outlet opening or discharge outlet of the bowl 11 to a drain or soil pipe. The passageway, or trapway, generally includes a first portion, a second portion, and a weir separating the first and second portions. The first portion of the passageway may extend from the outlet opening of the bowl 11 at an upwardly oblique angle to the weir. The second portion of the passageway may extend from the weir downwardly to the exiting device, such as the drain or soil pipe.

Between operational cycles (e.g., flush cycles) of the toilet 10, the water (and waste) is collected in the first portion of the trapway (in addition to the receptacle of the bowl), such that the weir prohibits the water from passing past the weir and into the second portion of the trapway. A flushing cycle may begin upon activation of the actuator. Upon activation of the actuator, additional water may be discharged into the bowl 11 through rim opening 15 and/or a sump jet, resulting in the flushing action and waste removal. For example, water may be discharged into the bowl from rim opening 15 along a swirling surface 16 on the interior of the bowl 11 below the rim 12. The swirling surface 16 forms a channel below the rim 12 so that water from the rim opening 15 travels along the channel forming a swirling motion to wash the inside of the bowl 11. The swirling motion is in a circular around the interior of the bowl 11. The swirling motion may be clockwise or counterclockwise as dictated by the direction of the rim opening 15.

Figure 2:
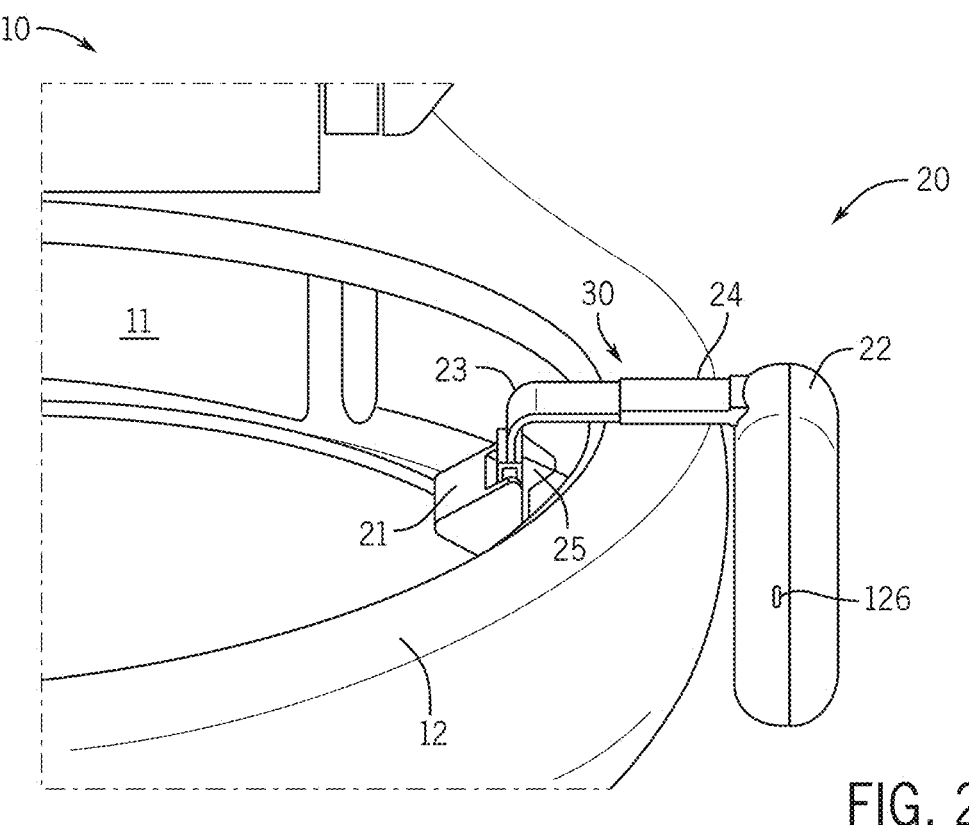
FIG. 2 illustrates toilet data collection device in an uncontracted position.
Figure 3:
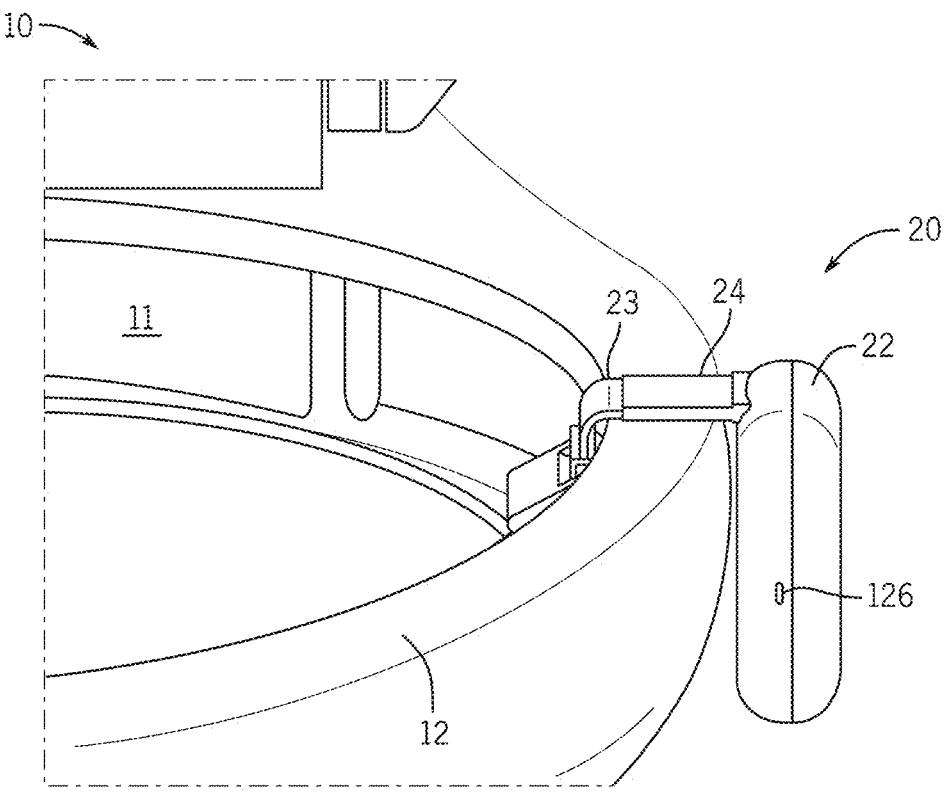
FIG. 3 illustrates toilet data collection device in a mounted position.

FIG. 1 illustrates the data collection device 20 above the toilet 10. For example, FIG. 1 illustrates a position that the user is holding the data collection device 20 above the toilet 10 before it is installed or mounted on the rim 12. FIG. 2 illustrates the data collection device 20 resting on the rim 12 but not yet secured to the rim 12. FIG. 3 illustrates the data collection device 20 secured to the rim 12. The inner extender 23 has been pushed inside the outer extender 24 to shorten the bridge 30 to fit tightly onto the rim 12.

The bumper 25 may be configured to space the first component 21 at a predetermined distance from the rim 12 and/or bowl 11. The predetermined distance may be sized such that the water traveling through the channel along the swirling surface 16 has sufficient space to maintain the swirling motion. In other words, the predetermined distance between the first component 21 and the rim 12 or bowl 11 is selected so that that the channel is large enough for sufficient water for rinsing the bowl 11 travels between the first component 21 and the bowl 11. The water in the channel travels between the first component 21 and the second compartment 22. A hypothetical line connecting the first component 21 and the second component 22 intersect the water in the channel along the swirling surface 16.

The bumper 25 may be formed from a variety of materials. The bumper 25 may be comprised of a rubber or a rubber like resin. For example, the bumper 25 may be comprised of a thermoplastic elastomer (TPE) such as thermoplastic vulcanizate (TPV), styrenic block copolymers (TPE-S), thermoplastic polyolefins (TPE-O), thermoplastic polyurethanes (TPE-U), thermoplastic copolyesters (TPE-E), melt processable rubber (MPR), thermoplastic polyether block amides (TPE-A), ethylene vinyl acetate (EVA) or a combination thereof. In some embodiments, the bumper 25 may be comprised of two or more materials. In one example, the bumper 25 may include a polypropylene (PP) shell and over molded with a rubber or rubber like resin. Accordingly, the grip performance of the bumper may be maximized.

The bumper 25 may be flexible. In some embodiments, the bumper 25 may configured to deform to set the predetermined distance to space the first component 21 from the rim 12 and/or bowl 11. The bumper 25 may be formed from a material or materials selected based on their durometer properties of the material.

Figure 4:
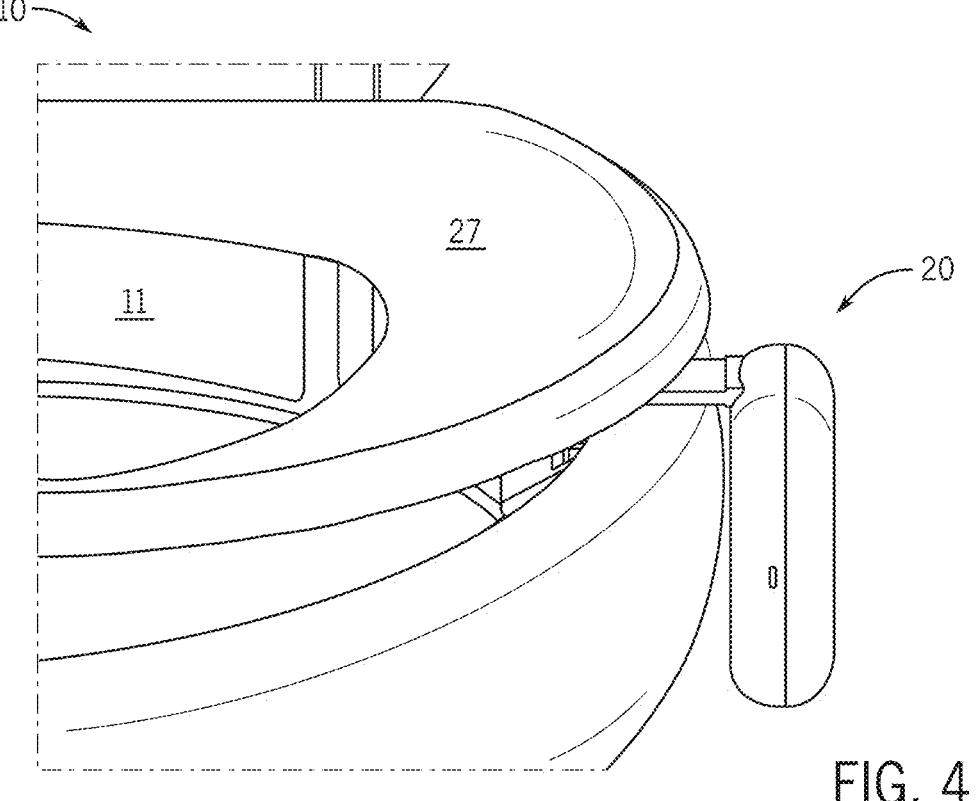
FIG. 4 illustrates toilet data collection device in a mounted position with a toilet seat placed over a bridge of the toilet data collection device.

FIG. 4 illustrates the data collection device 20 after the toilet seat 27 has been lowered over the bridge 30 of the data collection device 20. The toilet seat 27 may contact the bridge 30. The toilet seat 27 may include a recessed portion to receive the bridge 30. The bridge may be formed of a material having a predetermined brittleness or compressive strength such that the weight of the seat 27 and the human user sitting on the seat does not deform or otherwise damage the bridge. The bridge may have a height of 3-10 millimeters (e.g., 6 mm). The bridge 30 may also include a protective cushion, collar, or other structure to protect the bridge 30. The protective cushion may cover the bridge 30 with any of the materials described above with respect to the bumper 25. The collar may include at least one supporting arm or wall that contacts both the seat 27 and the rim 12 to support the seat 27 without placing substantial weight or stress on the bridge 30.

The first compartment 21 includes at least one circuit component and the second compartment 22 includes at least one circuit component. Various embodiments of the circuitry are described below. The bridge 30 includes wires, traces, or other conductors for provided power and/or communication between the circuitry of the first compartment 21 and that of the second compartment 22.

Because the bridge 30 changes size, by virtue of the relative movement of the inner extender 23 and the outer extender 24, the conductors should be adaptable. In some examples, the conductors may be provided by a ribbon cable that is configured to elongate or contract. In some examples, the conductors may be provided by looped or slacked wiring in the bridge such that the wires move within a cavity as the bridge 30 changes size. In some examples, the conductors may include traces on the inner extender 23 and the outer extender 24 that slide with respect to each other in a direction parallel so as to maintain the physical conduct and electrical conduct and the inner extender 23 is moved relative to the outer extender 24.

In other words, as the bridge 30 is adjusted in size, one or more electrical conductors (e.g., power connection and/or data connection) are also modified in respond to the adjustment in size of the bridge 30. In some examples, the one or more electrical conductors include a first electrical connection corresponding to a first size (e.g., reduced size) of the bridge 30 and a second electrical connection corresponding to a second size (e.g., extended size) of the bridge 30.

Figure 5:
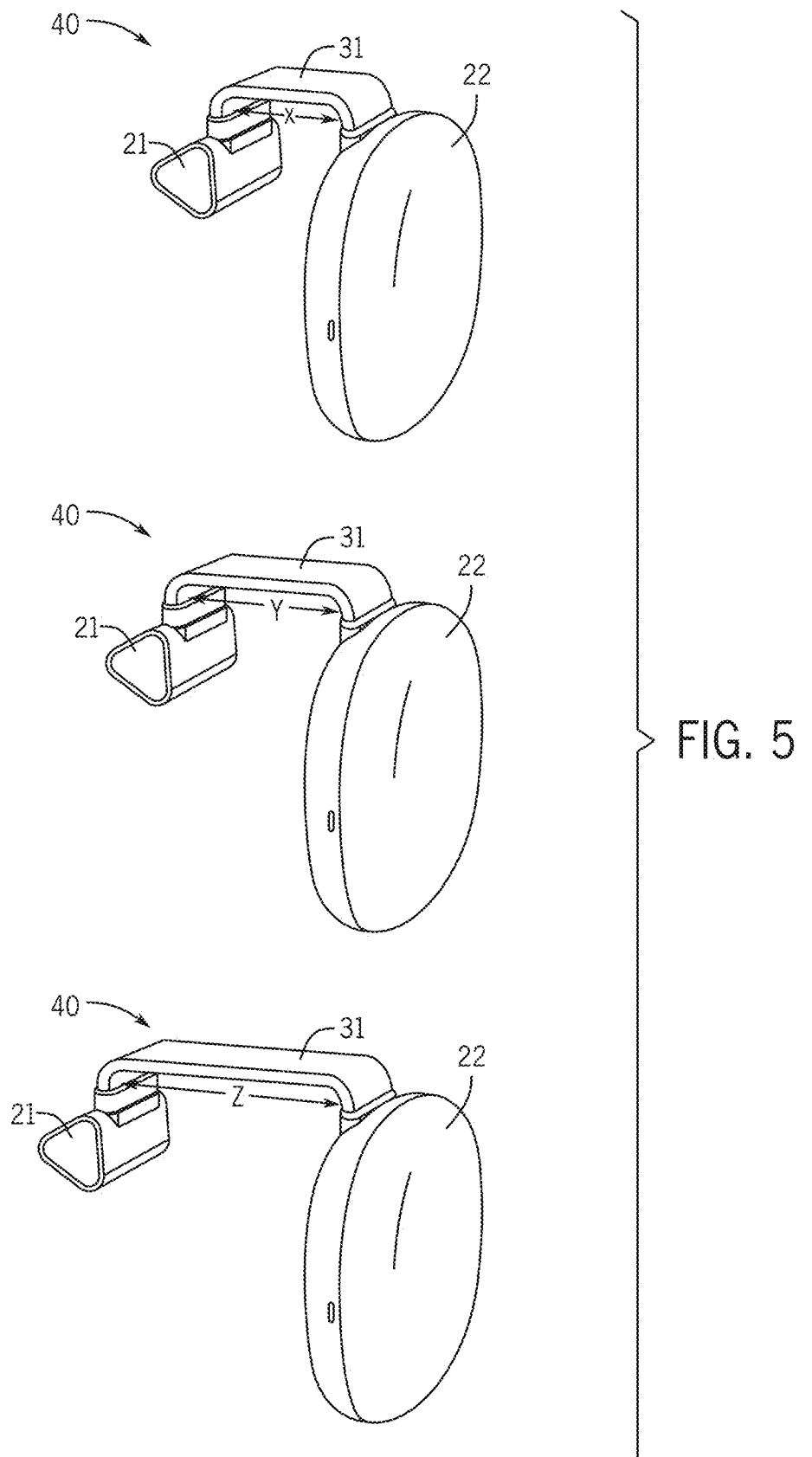
FIG. 5 illustrates three modular interchangeable bridges.

FIG. 5 illustrates three modular interchangeable bridges 31 including a small length X, a medium length Y, and a long length Z. As an example, the bridges 31 in FIG. 5 do not adjust in size; instead, the bridges 31 are removable, replaceable, modular, and interchangeable such that a bridge of a first sized may be removed and replaced with a bridge of a second size. The bridge 31 may be removable from the first compartment 21 and that of the second compartment 22. The bridge 31 may snap-fit into a recess in each of the first compartment 21 and that of the second compartment 22. The bridge 31 may fastened to the first compartment 21 and/or the second compartment 22 using a screw, a pin, a spring, or another fastener. The bridge 31 may be magnetically coupled to the first compartment 21 and/or the second compartment 22.

The user may interchange the bridge to select the bridge 31 that fits a specific rim 12. A particular size for the bridge 31 may be selected based on the width of the rim 12. For example, a user may measure the width of the rim 12 and place an order for the data collection device 20 having a bridge of the corresponding width. In one example, the user may place an order over the phone or website according to a particular model of toilet, and the size of the bridge is looked up according to the model of toilet.

Figure 6:
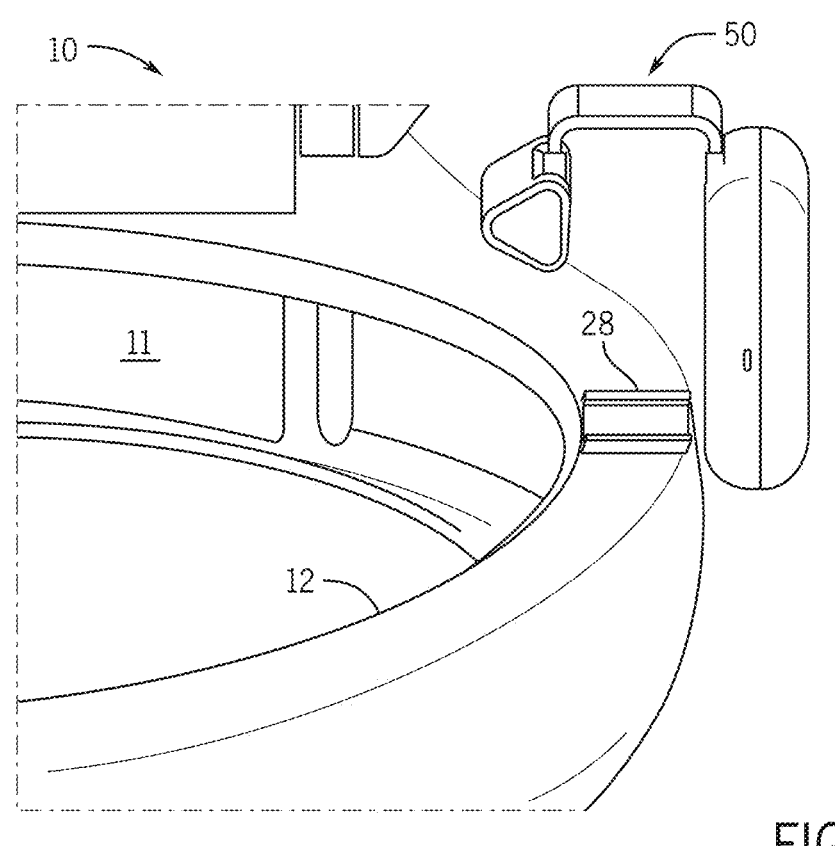
FIG. 6 illustrates a conforming bridge in an unmounted position.
Figure 7:
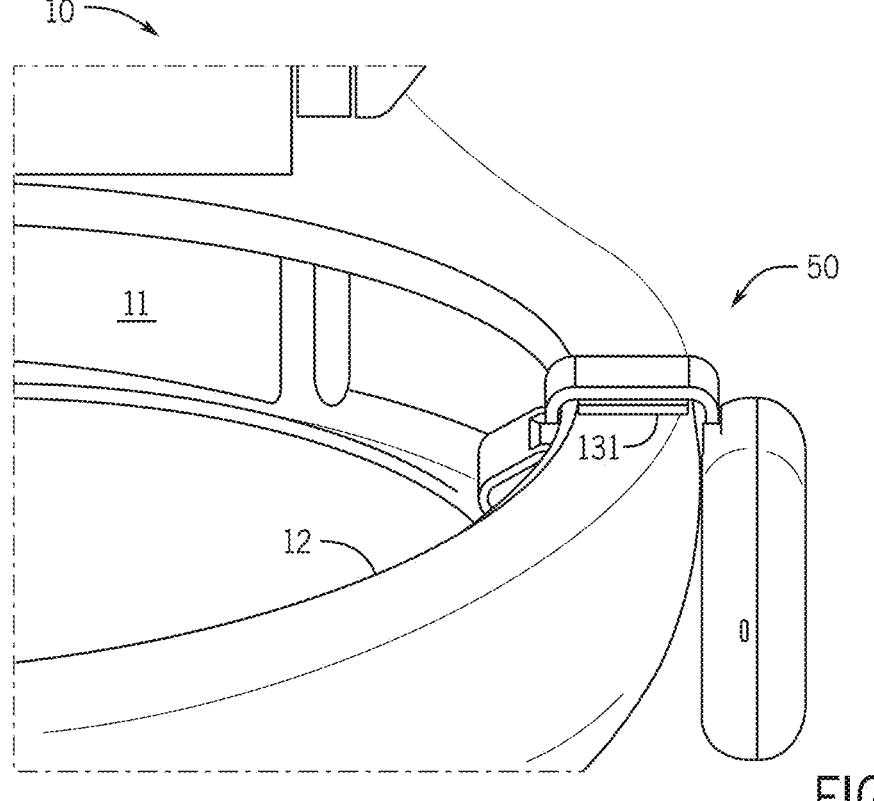
FIG. 7 illustrates a conforming bridge in a mounted position.

FIG. 6 illustrates a conforming bridge 50 in an unmounted position. FIG. 7 illustrates the conforming bridge 50 in a mounted position. The conforming bridge 50 is configured to change shape to be bended against the contours of the rim 12. The conforming bridge 50 may include a rigid but flexible metal strap surrounding by a plastic or resin. Additional, different, or fewer components may be included.

A cleat 28 may be attached directly to the rim 12. The conforming bridge 50 may rest on the cleat 28. The clear may include a magnet or magnetic material that attached a corresponding magnet or magnetic material in the conforming bridge 50. Alternatively, the cleat may include an adhesive or a tactile material.

Figure 8:
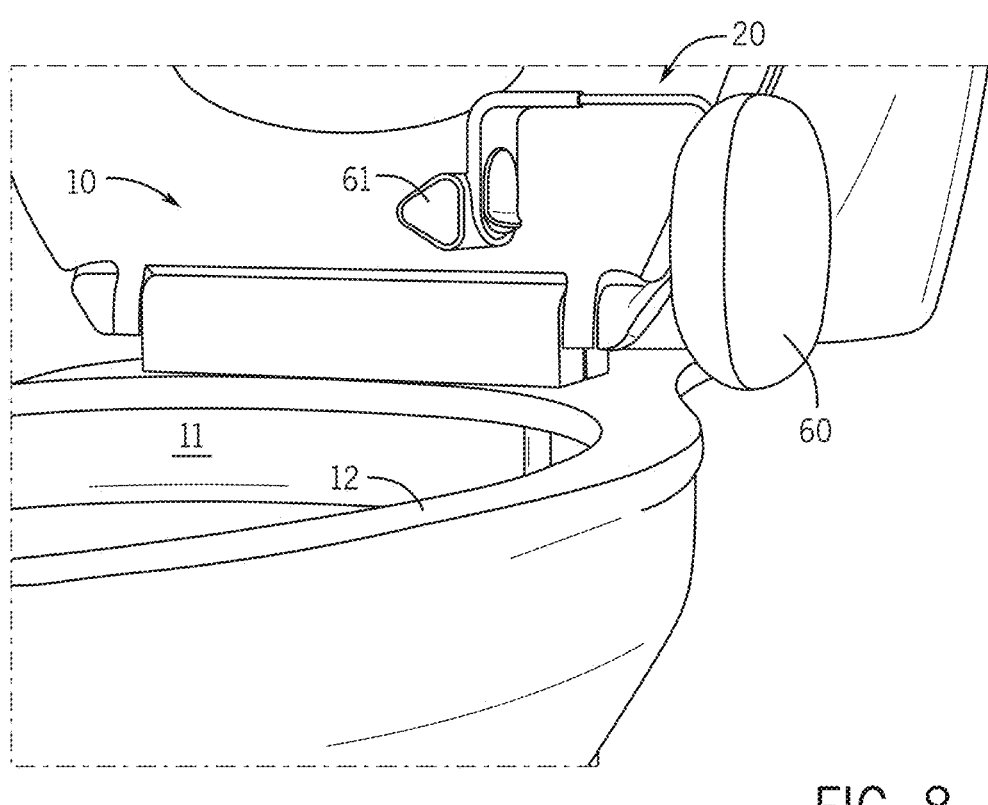
FIG. 8 illustrates an example puck style compartment.
Figure 9:
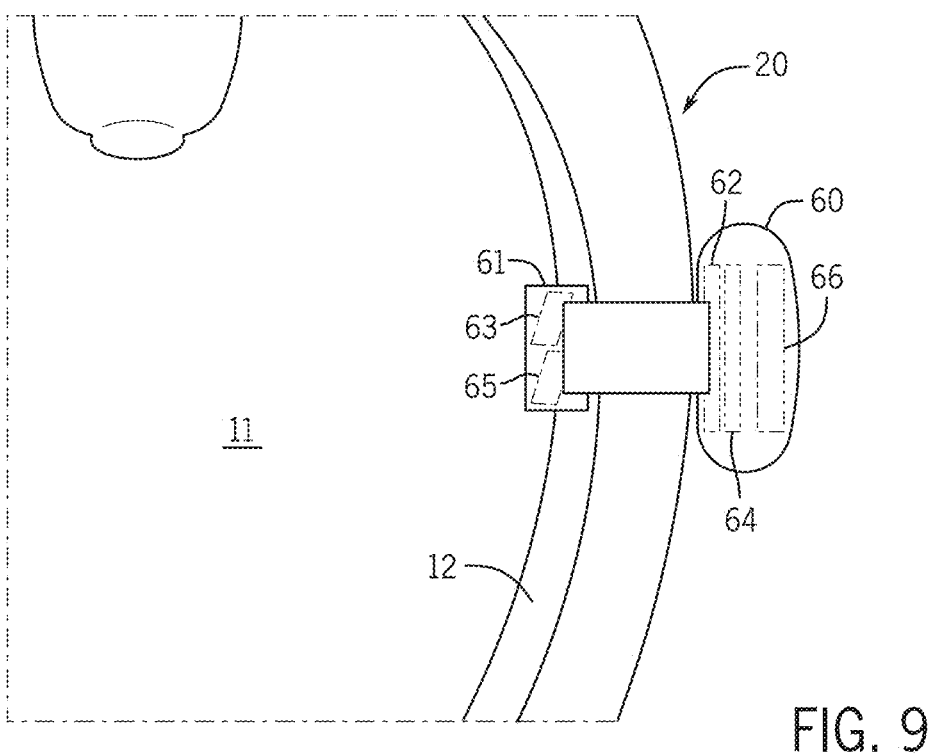
FIG. 9 illustrates an example circuit layout for the puck style compartment of FIG. 8.

FIG. 8 illustrates an example puck style compartment including a puck 60 connected to a sensor module 61. The puck 60 may have a shape of a cylinder or rounded rectangular prism. FIG. 9 illustrates an example circuit layout for the puck style compartment of FIG. 8. In this example, the sensor module 61 includes a sensor board 63 and a light emitting diode (LED) board 65. Additional, different, or fewer components may be included.

The sensor board 63 may include various sensors for the detection or measurement of urine or feces in the toilet 10. The sensors may include a camera. The LED board 65 may be coupled with a LED that projects light on to the urine, feces, or other contents of the toilet 10 to facilitate the collection of images (e.g., illuminate). In any of these examples, the camera may be configured to collect images of feces, urine, or other contents of the bowl 11. The sensor board 63 including the camera may collect data for spectroscopy. In any examples, the sensor board 61 receives or collects sensor data indicative of urine, feces, or another material deposited at the bowl 11.

The puck 60 may include a driver board 62, a battery 66, and a controller 64 arranged in at least two layers parallel to the circumference of the rim 12, as shown in FIG. 9. The controller 64 may include a microcontroller chip, a flash memory, and a universal serial bus (USB) port 126 for power, data, and programming. The controller 64 may also include a serial wire debug (SWD) port for troubleshooting and monitoring. The driver board 62 may include such ports and memory for programming the controller 64. The driver board 62 may be omitted.

The battery 66 is in a separate layer in the puck 60, the controller 64 is in a separate layer in the puck 60, and the driver board 62 is in a separate layer in the puck 60. The controller 64 may be configured to analyze images collected by the camera. The controller 64 may identify one or more medical conditions or other measurements from the images.

The controller 64 receives sensor data from the sensor board 61 through one or more data connection through the bridge 30. The controller 64 may compare the sensor data from the sensor board 61 to one or more thresholds or templates to determine when a predetermined condition has occurred. The threshold or template may be stored in memory. In some example, the controller 64 identifies the presence of the urine and/or feces in addition to identification of the predetermined condition.

Figure 10:
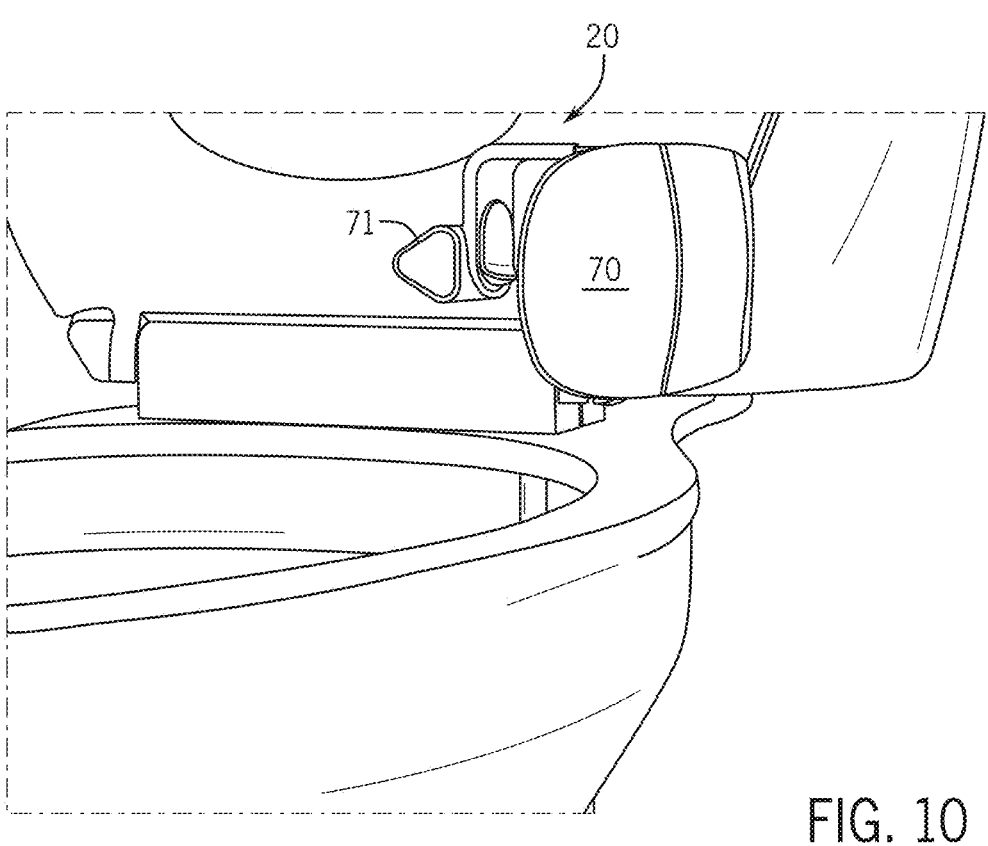
FIG. 10 illustrates an example outer curve style compartment.
Figure 11:
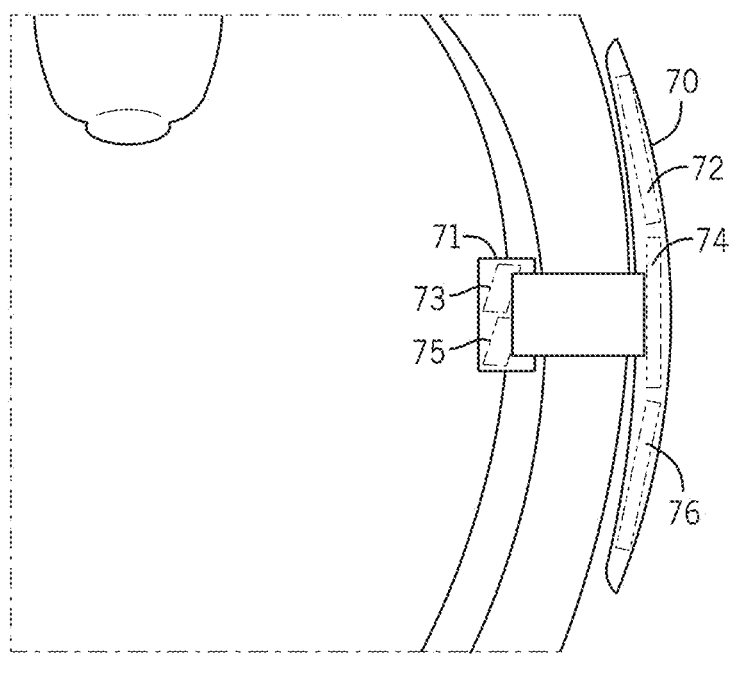
FIG. 11 illustrates an example circuit layout for the outer curve style compartment of FIG. 10.

FIG. 10 illustrates an example outer curve style compartment including an outer curve compartment 70 and a sensor module 71. FIG. 11 illustrates an example circuit layout for the outer curve style compartment of FIG. 10. In this example, the outer curve compartment 70 includes a driver card 72, a battery 76, and a controller 74 arranged in a single layer parallel to the rim 12. The sensor module 71 includes a sensor board 73 and a LED driver board 75. Additional, different, or fewer components may be included.

The controller 74 receives sensor data from the sensor module 71 through one or more data connection through the bridge 30. The controller 74 may compare the sensor data from the sensor module 71 to one or more thresholds or templates to determine when a predetermined condition has occurred. The threshold or template may be stored in memory. In some example, the controller 74 also identifies the presence of the urine and/or feces in addition to identification of the predetermined condition.

Alternatively, the sensor data from the sensor module 71 may be transmitted to the controller 74 wireless. For example, radio waves, a cellular telephone network, an 802.11, 802.16, 802.20, or WiMax network, a Bluetooth pairing of devices, or a Bluetooth mesh network may be used to transmit the sensor data from the sensor module 71 to the controller 74.

Figure 12:
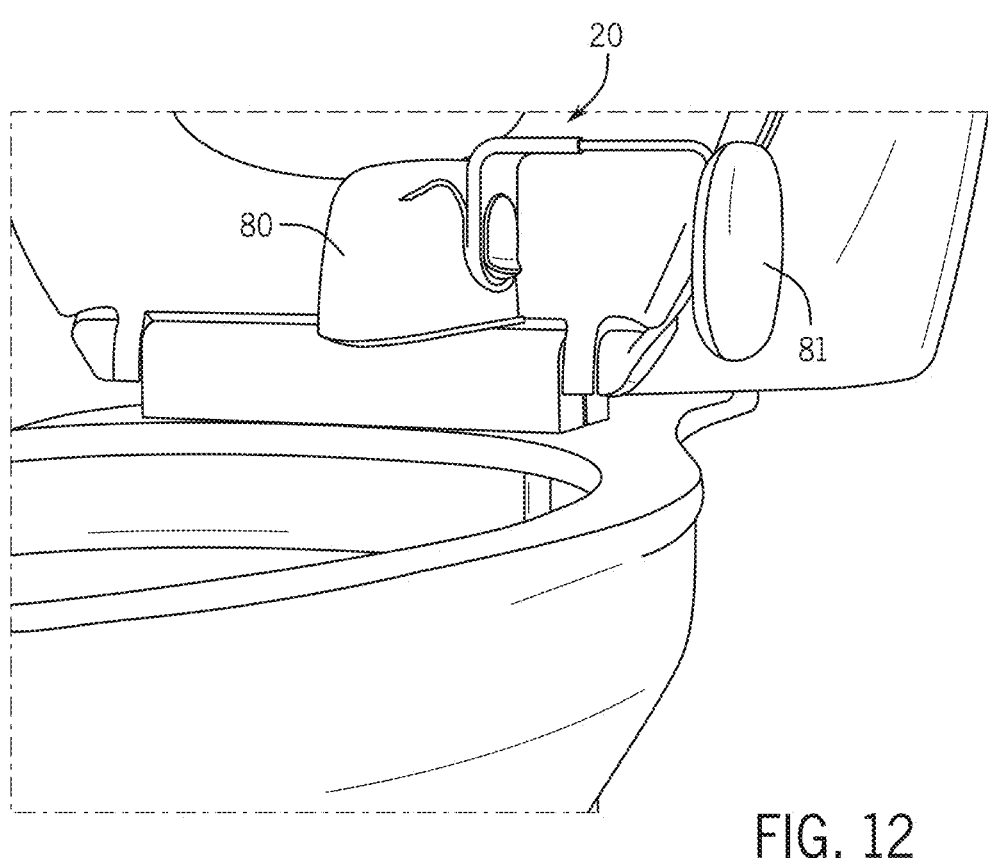
FIG. 12 illustrates an example inner curve style compartment.
Figure 13:
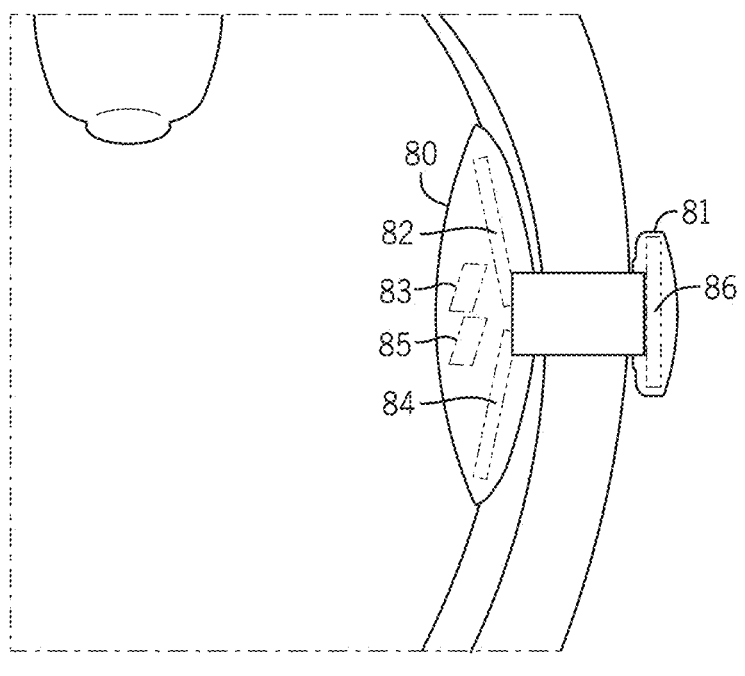
FIG. 13 illustrates an example circuit layout for the inner curve style compartment of FIG. 12.

FIG. 12 illustrates an example inner curve style compartment including an inner curve component 80 and battery module 81. FIG. 13 illustrates an example circuit layout for the inner curve style compartment of FIG. 12. The inner curve component 80 may include a sensor board 83, a light board 85, a driver card 82, and a controller 84. The battery module 81 may include only a battery 86. Additional, different, or fewer components may be included.

In the example of FIG. 12, only electrical connections are provided between the battery module 81 and the inner curve component 80. That is, the bridge 30 includes at least one electrical connection between the battery module 81 and the inner curve component 80 but does not include any data connection between the battery module 81 and the inner curve component 80. Instead, the sensor board 83 and the controller 84 are co-located in the inner curve component 80 and communication through a direct connection (e.g., wire or printed circuit board).

The controller 84 receives sensor data directly from the sensor board 83. The controller 84 may compare the sensor data from the sensor board 83 to one or more thresholds or templates to determine when a predetermined condition has occurred. The threshold or template may be stored in memory. In some example, the controller 84 identifies the presence of the urine and/or feces in addition to identification of the predetermined condition.

In any of these examples, the battery (e.g., the battery module) may include two batteries. One battery may be a removable battery, and one battery may be permanent. The removable battery may provide the primary source of power for the sensor board, the light board, the driver card, the battery, and the controller. The removable battery may be removed from the collection device 20 and charged via a wire and outlet, induction, or another technique. The permanent battery provides power to at least one of the sensor board, the light board, the driver card, the battery, and the controller when the removable battery has been removed for charging. In this way there is potentially always a source of power for the data collection device.

Any of these embodiments of the data collection device may also include a user identification module. The user identification module may include a fingerprint reader. The user identification module may include a near field communication or radio frequency identification that interacts with a mobile device or a tag of the user. The user identification module generates data indicative of the user's identity (e.g., a username, a code, or an alphanumeric word) and sends the identifier (e.g., sometimes through the electrical conductors of the bridge) to the controller. The controller may store analyzed biometric data in a memory in association with the identifier of the user. The controller (e.g., via a communication interface) may also transmit the analyzed biometric device paired with the user identifier to another device such as a server, a mobile device, or a network device.

Figure 14:
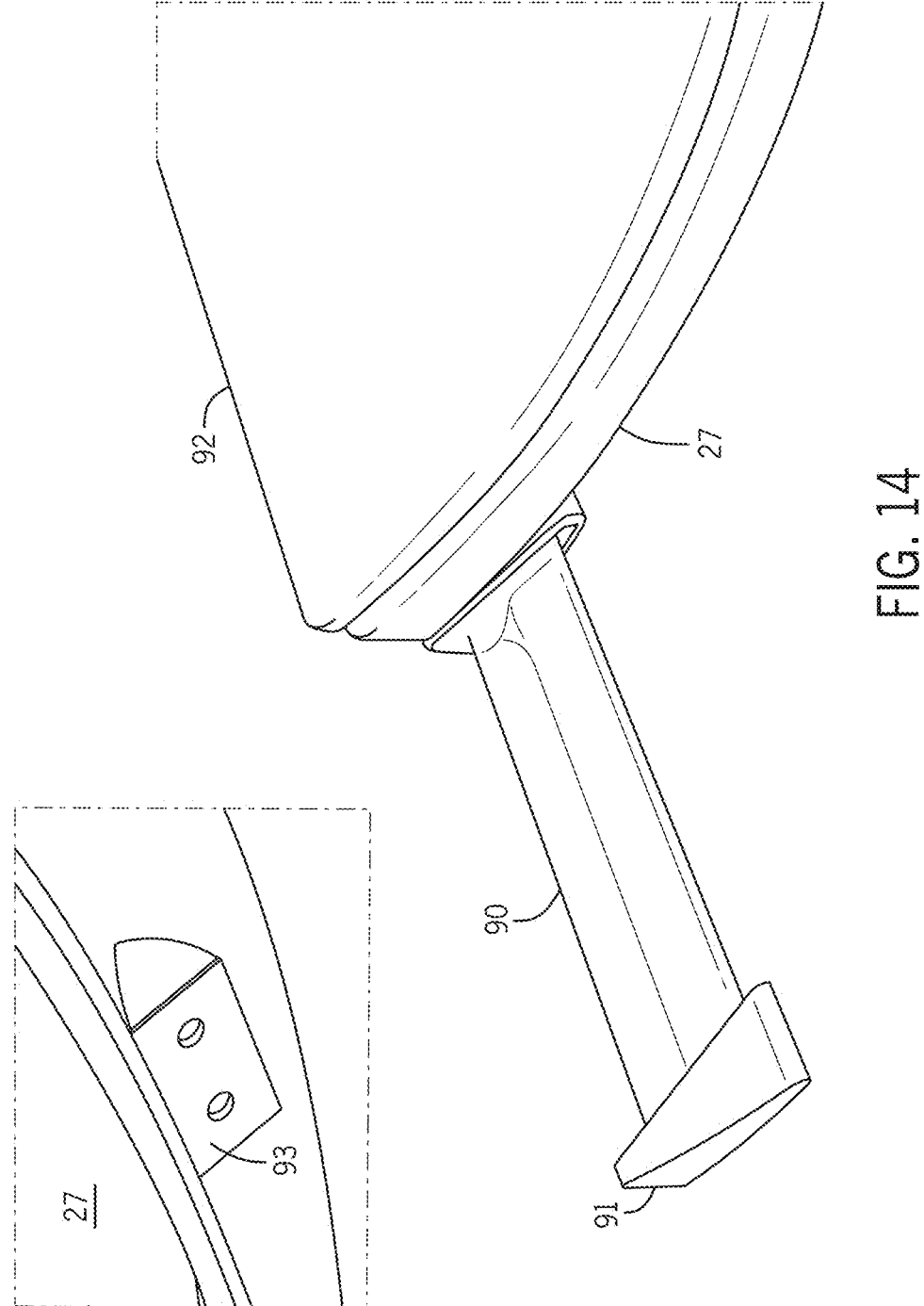
FIG. 14 illustrates an example seat compartment for the data collection device.

FIG. 14 includes another embodiment including a biometric data collection device embedded in the toilet seat 27. Circuitry 90 may include any combination of a sensor board, a light board, a driver card, a battery, and a controller. The circuitry 90 is configured to slide in and out of the toilet seat

27 using a handle or latch 91. The collection sensor 93 (e.g., camera) may be mounted on an underside of the toilet seat 27.

Figure 15:
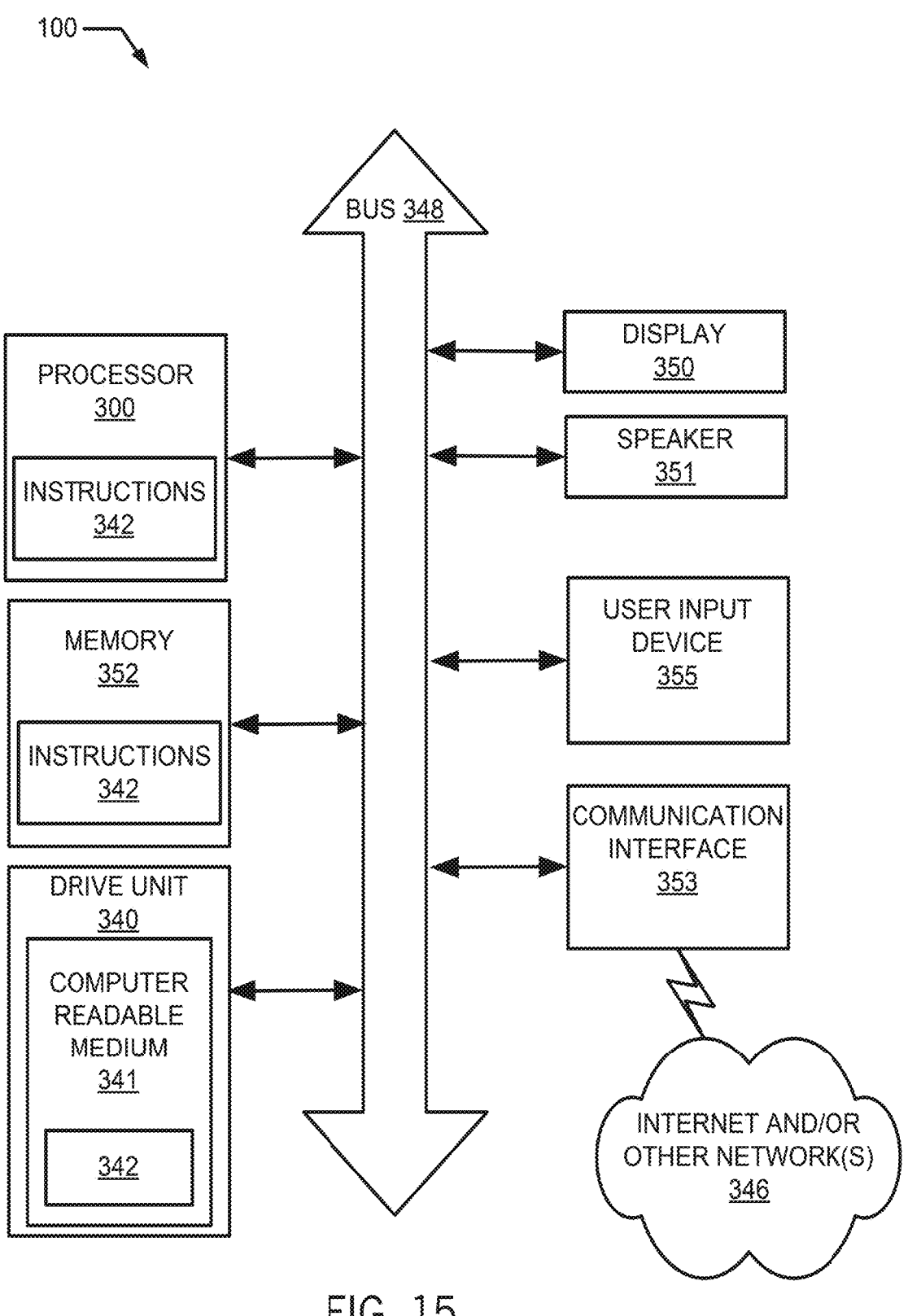
FIG. 15 illustrates an example controller for any of the disclosed embodiments.

FIG. 15 illustrates an example control system or controller 100 for any of the embodiments described herein. The controller 100 may include a processor 300, a memory 352, and a communication interface 353 for interfacing with devices or to the internet and/or other networks 346. In addition to the communication interface 353, a sensor interface may be configured to receive data from the sensors described herein or data from any source. The controller 100 may include an integrated display 350, speaker 351, or other output devices. The components of the control system may communicate using bus 348. The control system may be connected to a workstation or another external device (e.g., control panel) and/or a database for receiving user inputs, system characteristics, and any of the values described herein.

Figure 16:
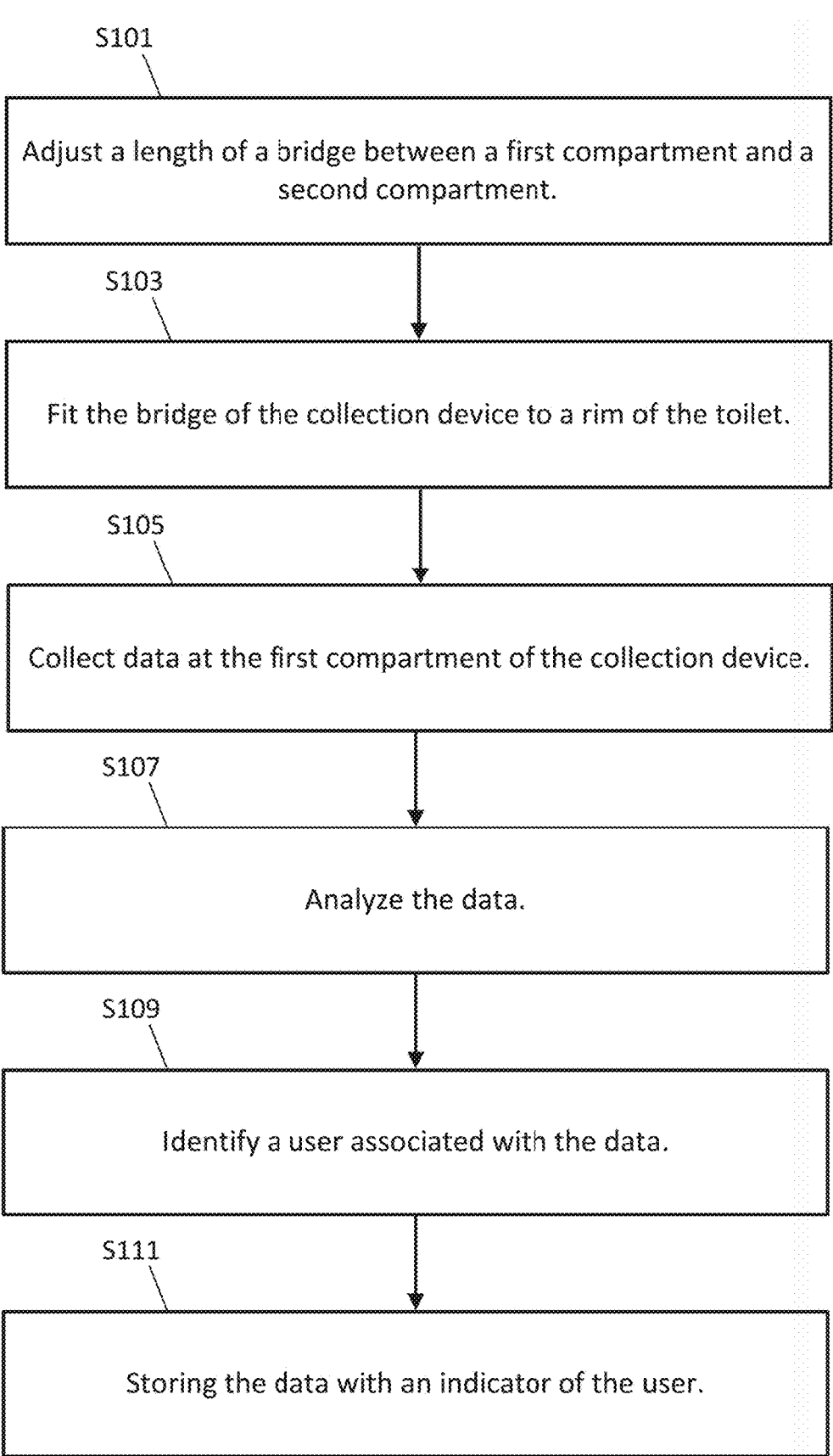
FIG. 16 illustrates an example flow chart for the controller of FIG. 15.

FIG. 16 illustrates an example flow chart for the operation of the biometric data collection device. Additional, different, or fewer acts may be performed.

At act S101, a length of a bridge between a first compartment and a second compartment of a biometric data collection device is adjusted. The length may be adjusted using a spring clamp, module bridge extenders, or a conformable bridge.

At act S103, the biometric data collection device is fit to a rim of the toilet. For example, after adjustment of the length of the bridge to fir the rim, the user may place the collection device on the rim.

Once installed on the rim, the collection device may be turned on to commence the collection of data. At act S105, the sensor collects data at the first compartment of the biometric data collection device. At act S107, the controller analyzes the data. At act S109, an identification module including another sensor identifies a user associated with the data. At act S111, the controller stores the data with an indicator of the user in memory or transmits the analyzed data and indicator to another device.

Optionally, the control system may include an input device 355 and/or a sensing circuit 356 in communication with any of the sensors. The sensing circuit receives sensor measurements from sensors as described above. The input device may include any of the user inputs such as buttons, touchscreen, a keyboard, a microphone for voice inputs, a camera for gesture inputs, and/or another mechanism.

Optionally, the control system may include a drive unit 340 for receiving and reading non-transitory computer media 341 having instructions 342. Additional, different, or fewer components may be included. The processor 300 is configured to perform instructions 342 stored in memory 352 for executing the algorithms described herein. A display 350 may be an indicator or other screen output device. The display 350 may be combined with the user input device 355.

Processor 300 may be a general purpose or specific purpose processor, an application specific integrated circuit (ASIC), one or more programmable logic controllers (PLCs), one or more field programmable gate arrays (FPGAs), a group of processing components, or other suitable processing components. Processor 300 is configured to execute computer code or instructions stored in memory 352 or received from other computer readable media (e.g., embedded flash memory, local hard disk storage, local ROM, network storage, a remote server, etc.). The processor

300 may be a single device or combinations of devices, such as associated with a network, distributed processing, or cloud computing.

Memory 352 may include one or more devices (e.g., memory units, memory devices, storage devices, etc.) for storing data and/or computer code for completing and/or facilitating the various processes described in the present disclosure. Memory 352 may include random access memory (RAM), read-only memory (ROM), hard drive storage, temporary storage, non-volatile memory, flash memory, optical memory, or any other suitable memory for storing software objects and/or computer instructions. Memory 352 may include database components, object code components, script components, or any other type of information structure for supporting the various activities and information structures described in the present disclosure. Memory 352 may be communicably connected to processor 300 via a processing circuit and may include computer code for executing (e.g., by processor 300) one or more processes described herein. For example, the memory 352 may include graphics, web pages, HTML files, XML files, script code, shower configuration files, or other resources for use in generating graphical user interfaces for display and/or for use in interpreting user interface inputs to make command, control, or communication decisions.

In addition to ingress ports and egress ports, the communication interface 353 may include any operable connection. An operable connection may be one in which signals, physical communications, and/or logical communications may be sent and/or received. An operable connection may include a physical interface, an electrical interface, and/or a data interface. The communication interface 353 may be connected to a network. The network may include wired networks (e.g., Ethernet), wireless networks, or combinations thereof. The wireless network may be a cellular telephone network, an 802.11, 802.16, 802.20, or WiMax network, a Bluetooth pairing of devices, or a Bluetooth mesh network. Further, the network may be a public network, such as the Internet, a private network, such as an intranet, or combinations thereof, and may utilize a variety of networking protocols now available or later developed including, but not limited to TCP/IP based networking protocols.

While the computer-readable medium (e.g., memory 352) is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored. The computer-readable medium may be non-transitory, which includes all tangible computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

Figure 17:
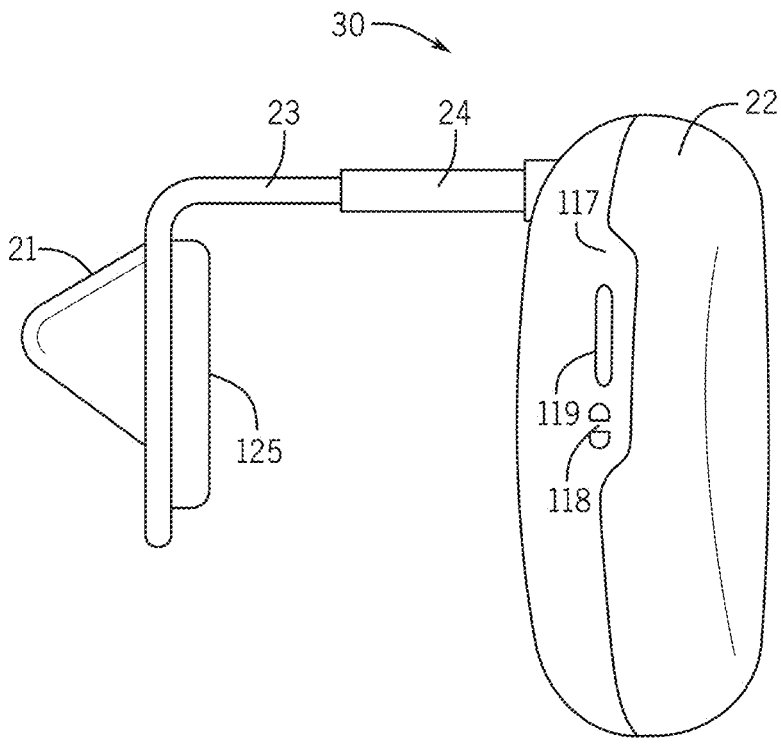
FIG. 17 illustrates another embodiment of the data collection device.

FIG. 17 illustrates another embodiment of the data collection device 30, including the first compartment 21 and the second compartment 22. The first compartment 21 is coupled to the second compartment 22 by the bridge 30 including the inner extender 23 fits within the outer extender 24. In addition to port 126 described above, the data collection device 30 may include a window 118 adjacent to a sensor (e.g., motion sensor) configured to detect movement of the user or gestures from the user. The data collection device 30 may include a window 117 adjacent to a light (e.g., LED) that indicates power operation or a mode or the data collection device 30. The data collection device 30 may include one or more buttons or inputs 119 to select a mode or turn on/off the data collection device 30. Additional, different, or fewer components may be included.

The grip/bumper described above may be replaced with a swappable pad 125. FIGS. 18A-C illustrates the swappable pad for the data collection device in a rear view (FIG. 18A), a side view (FIG. 18B), and a front view (FIG. 18C). The swappable pad 125 may include an outer cover 126 and an inner core 127 that are coupled together.

The swappable pad 125 includes at least one magnet 121. The magnet 121 is configured to align the swappable pad 125 with the first components at a predetermined angle. The swappable pad 125 includes a ridge 128 which is configured to space the first compartment 21 from the rim 11. The magnet 121 allows the swappable pad 125 to easily be removed and replaced with a new swappable pad. The first component 21 may include another magnet or magnetizable material to selectively couple with the magnet 121. Different swappable pads may be used with different models of the data collection device 30 and/or different models of the toilet 10.

The swappable pad 125 may be formed from a variety of materials are described herein with respect to the bumper 25 (e.g., resins, elastomers, rubbers, etc.)

Figure 19C:
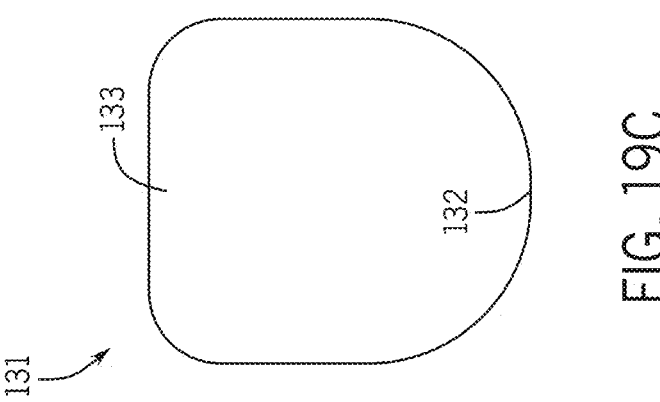
FIGS. 19A-C illustrates another swappable pad for the data collection device.
Figure 19B:
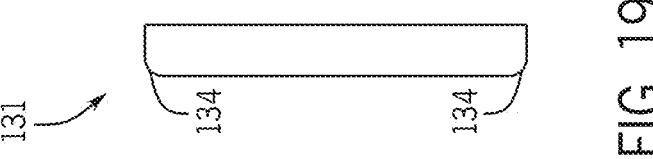
Figure 19A:
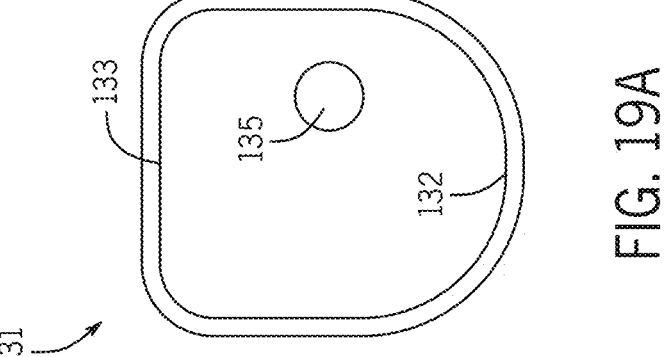

FIGS. 19A-C illustrates another swappable pad for the data collection device. A spacer 131 may be used as cleat 28 to space the bridge 31 from the rim 12. FIGS. 19A-C include multiple views for the spacer 131 including rear view (FIG. 18A), a side view (FIG. 18B), and a front view (FIG. 18C).

The spacer 131 may include a rounded side 132 and a flat side in a horizontal direction (e.g., parallel to the rim 12). The spacer 131 may also include rounded edges 134. The spacer 131 may be formed of a rigid material. The spacer 131 may optionally include a magnet 135 for selectively coupling the spacer 131 to the bridge 31, which includes an opposing magnet or magnetic material.

Figure 20:
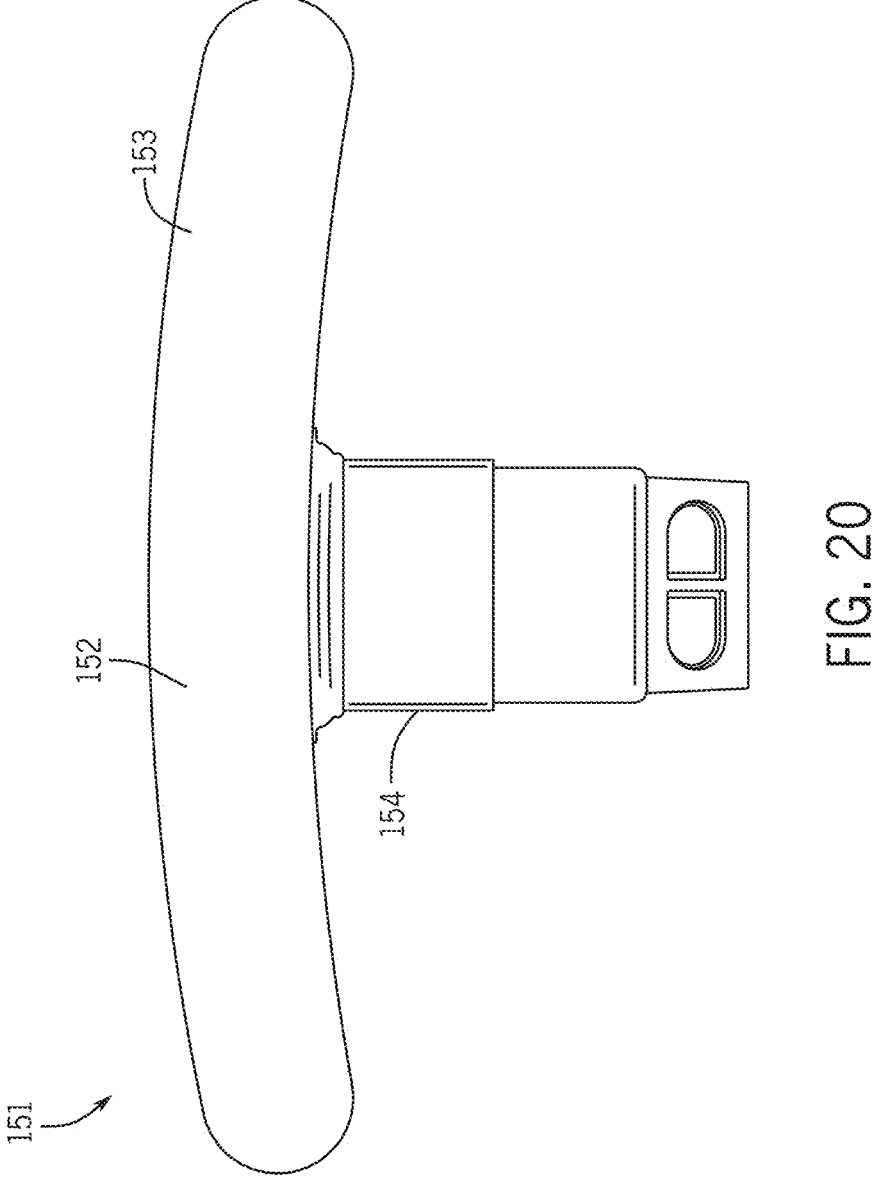
FIG. 20 illustrates another embodiment of the data collection device.

FIG. 20 illustrates another embodiment of a data collection device 151. The data collection device 151 may include multiple portions including a controller compartment 152 and a battery 153. A coupling device is configured to couple the data collection device 151 to the battery 153. An electrical connections provides power from the battery 153 to the compartment 152.

The bridge 30 may also include an identifier or indicia 154 that identifies the data collection device 151. The indicia may also include manufacturer device, compatible toilets, or other information.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope and spirit of the following claims and equivalents thereto are claimed as the invention.

What is claimed is:

1. A biometric data collection device for a toilet, the biometric data collection device comprising:
   a first compartment including a first circuit board;
   a second compartment including a second circuit board; and
   a bridge coupled to the first compartment and the second compartment and configured to be supported by a rim of the toilet so that the first compartment is inside of a bowl of the toilet and the second compartment is outside of the bowl of the toilet, wherein the bridge is changeable in length to fit different widths of the rim.

2. The biometric data collection device of claim 1, further comprising:
   a camera configured to collect images from inside the bowl, wherein the first circuit board is electrically coupled to the camera.

3. The biometric data collection device of claim 1, further comprising:
   a battery electrically coupled to the second circuit board.

4. The biometric data collection device of claim 1, further comprising:
   a light coupled to the first circuit board.

5. The biometric data collection device of claim 1, further comprising:
   a communication interface coupled to the second circuit board.

6. The biometric data collection device of claim 1, wherein the bridge is deformable against the rim of the toilet.

7. The biometric data collection device of claim 1, wherein the bridge includes a modular extender removable from the first compartment and the second compartment.

8. The biometric data collection device of claim 1, wherein the bridge includes an outer extender and an inner extender configured to extend within the outer extender.

9. The biometric data collection device of claim 8, further comprising:
   a spring to cause the inner extender to extend within the outer extender.

10. The biometric data collection device of claim 8, further comprising:
   a conductor configured to change a length of an electrical path based on a relative position of the inner extender and the outer extender.

11. The biometric data collection device of claim 1, further comprising:
   a battery module including a removable battery and a nonremovable battery.

12. The biometric data collection device of claim 11, wherein the nonremovable battery provides power to the first circuit board or the second circuit board when the removable battery is removed.

13. The biometric data collection device of claim 11, wherein the removable battery is configured to charge the nonremovable battery.

14. The biometric data collection device of claim 1, further comprising:
   a controller configured to analyze data from the first circuit board.

15. The biometric data collection device of claim 14, further comprising:
   a user identification sensor configured to identify a user associated with the toilet, wherein the controller is configured to store the analyzed data according to the user.

16. A toilet having biometric data collection, the toilet comprising:

a rim having a set width;

a first compartment including a first circuit board;

a second compartment including a second circuit board; and a bridge coupled to the first compartment and the second compartment and configured to be supported by the rim of the toilet so that the first compartment is inside of a bowl of the toilet and the second compartment is outside of the bowl of the toilet, wherein the bridge is changeable in length to fit the set width of the rim.

17. The toilet of claim 16, wherein the bridge includes a conductor between the first circuit board and the second circuit board.

18. The toilet of claim 17, wherein the conductor is configured to change length in cooperation with the bridge.

\* \* \* \* \*